United States Patent [19]

Faler et al.

[11] 4,424,283

[45] Jan. 3, 1984

[54] CATALYST FOR SYNTHESIZING BISPHENOL AND METHOD FOR MAKING SAME

[75] Inventors: Gary R. Faler; Geroge R. Loucks, both of Scotia, N.Y.

[73] Assignee: General Electric Company, Schenectady, N.Y.

[21] Appl. No.: 342,435

[22] Filed: Jan. 25, 1982

Related U.S. Application Data

[60] Continuation-in-part of Ser. No. 252,493, Apr. 8, 1981, abandoned, Division of Ser. No. 103,095, Dec. 13, 1979, Pat. No. 4,294,995.

[51] Int. Cl.³ .......................... B01J 20/26; B01J 39/20
[52] U.S. Cl. ...................................... 521/32; 526/288; 525/355; 525/344; 525/333.5; 525/333.6
[58] Field of Search .................. 525/355; 526/288; 521/32

[56] References Cited

U.S. PATENT DOCUMENTS 3,394,089  7/1968  McNutt et al. ...................... 521/33
4,346,247  8/1982  Faler et al. ........................... 521/32

FOREIGN PATENT DOCUMENTS 23325  7/1979  European Pat. Off. .
2931036  2/1981  Fed. Rep. of Germany .

OTHER PUBLICATIONS

S. N. 273,005 C.I.P. of S. N. 172,936 Filing Date, 7/28/80 U.S. 7/31/79 W. German Priority.

*Primary Examiner*—Joseph L. Schofer
*Assistant Examiner*—Peter F. Kulkosky
*Attorney, Agent, or Firm*—William A. Teoli; James C. Davis, Jr.; James Magee, Jr.

[57] ABSTRACT

A sulfonated organic polymer, such as a sulfonated polystyrene ion-exchange resin is provided having organic mercaptan groups attached to backbone sulfone radicals by covalent nitrogen-sulfur linkages. A method for making such sulfonated organic polymer is also provided. The ion-exchange resin can be used to effect phenol-ketone condensation in the synthesis of bisphenols.

16 Claims, No Drawings

CATALYST FOR SYNTHESIZING BISPHENOL AND METHOD FOR MAKING SAME

CROSS REFERENCE TO RELATED APPLICATIONS

This application is a continuation-in-part of our copending application Ser. No. 252,493, filed Apr. 8, 1981, now abandoned which is a division of Ser. No. 103,095, filed Dec. 13, 1979, now U.S. Pat. No. 4,294,995. Reference also is made to the copending application of Gary R. Faler, for Method and Catalyst for Making Bisphenol, Ser. No. 298,711, filed Sept. 2, 1981, which is a continuation-in-part of application Ser. No. 192,447, filed Sept. 9, 1980, now abandoned, where all of the aforementioned applications are assigned to the same assignee as the present invention.

BACKGROUND OF THE INVENTION

Prior to the present invention, various methods were employed to synthesize bisphenols, such as bisphenol-A, by effecting reaction between a ketone and a phenol. One procedure, for example, involved the use of large amounts of inorganic acid catalysts, such as sulfuric acid or hydrochloric acid. Experience has shown, however, that the use of inorganic acids requires a means to remove such acids at the end of the reaction due to the corrosive action of the strong acids. In addition, distillation of the resulting bisphenol was often required because of the many by-products formed during the reaction under high acid conditions.

An improved procedure was developed by using a solid resin cation-exchange catalyst to effect the condensation between the phenol and the ketone. However, the disadvantage of the ion-exchange catalyst is the low acid concentration it provides resulting in the need for a rate accelerator such as a mercaptan. One procedure is shown by McNutt et al, U.S. Pat. No. 3,394,089, which incorporates the mercaptan by partial neutralization of the ion-exchange catalyst in the form of a sulfonated insoluble polystyrene resin. Another procedure involves the partial esterification of such sulfonic acid moiety with an alkyl mercapto alcohol, as shown by Apel et al, U.S. Pat. No. 3,153,001. A further procedure is shown by Wagner et al, U.S. Pat. No. 3,172,916, based on the partial reduction of the sulfonic acid to afford thiophenol functional groups. It has been found, however, that Wagner et al do not afford a particularly active type of mercaptan promoted catalyst for synthesizing bisphenols, such as bisphenol-A, while the methods of Apel et al and McNutt et al are susceptible to chemical degradation.

The present invention is based on the discovery that an organoaminodisulfide of the formula,

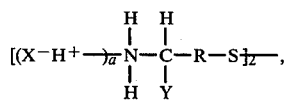

where R is a divalent $C_{(1-13)}$ organic radical, Y is selected from hydrogen, carboxy and nitrile, X is selected from halogen or a counter ion, and a is 0 or 1, can be used to make sulfonated polyaromatic organic polymer having organomercaptan groups covalently attached to sulfone radicals by nitrogen-sulfur linkages. An organomercaptan activated sulfonated aromatic ion-exchange resin is formed capable of resisting the leaching of organomercaptan normally shown by the organomercaptan sulfonated aromatic ion-exchange resins of the prior art. It has been found that after chemical attachment of the organoaminodisulfide of formula (1), the polymer can be reduced with a reducing agent such as triorganophosphine whereby the disulfide is converted to the mercaptan after acidification.

STATEMENT OF THE INVENTION

There is provided by the present invention, a method for making a leach resistant organomercaptan substituted sulfonate aromatic organic polymer which comprises, (1) effecting reaction between
 (A) a halosulfonated aromatic organic polymer, and
 (B) an organoaminodisulfide in the presence of base to produce a sulfonated aromatic organic polymer having organoaminodisulfide groups covalently attached to sulfone radicals by nitrogen-sulfur linkages, (2) effecting the reduction of the organoaminodisulfide groups on the sulfonated aromatic organic polymer of (1), and (3) recovering sulfonated aromatic organic polymer from (2) having covalently bonded organomercaptan groups attached to sulfone radicals by nitrogen-sulfur linkages.

In a further aspect of the present invention there is provided sulfonated aromatic organic polymer which is effective as a bisphenol catalyst based on phenol-ketone condensation, consisting essentially of divalent sulfonated aromatic organic units having organoaminomercaptan groups covalently attached to sulfone radicals by nitrogen-sulfur linkages of the formula,

chemically combined with divalent sulfonated aromatic units of the formula,

where R and Y are as previously defined, and $R^2$ is a trivalent $C_{(6-13)}$ aromatic organic radical.

As utilized in the description of the invention, the expression "sulfonated polyaromatic organic material having organoaminomercaptan groups covalently attached to sulfone radicals by nitrogen-sulfur linkages", means either a sulfonated aromatic organic polymer consisting essentially of formula (2) units chemically combined with formula (3) units, or a blend of such sulfonated aromatic organic polymer with sulfonated aromatic organic polymer which consists essentially of solely chemically combined units of formula (3). Those skilled in the art also would know however, that the term "sulfonated aromatic organic polymer" also can include chemically combined aromatic organic units of the formula, where $R^3$ is a divalent $C_{(6-13)}$ aromatic organic radical.

Most preferably, the sulfonated polyaromatic organic material can contain from about 4 mole percent to about 40 mole percent of chemically combined divalent sulfonated aromatic organic units of formula (2) having organoaminomercaptan groups attached to sulfone radicals by nitrogen-sulfur linkages. The sulfonated aromatic organic polymer utilized in the practice of the present invention to make the aforedescribed sulfonated polyaromatic organic material having organoaminomercaptan groups attached to sulfone raadicals by nitrogen-sulfur linkages, can consist essentially of from about 5 to about 95 mole percent of divalent aromatic organic units of formula (4), chemically combined with from about 95 mole percent to 5 mole percent of divalent sulfonated aromatic organic units of formula (3).

Radicals included by R of formulas 1 and 2 are $C_{(1-13)}$ alkylene radicals, for example, methylene, ethylene, propylene, butylene, pentylene, etc.; aromatic radicals, for example, phenylene, xylylene, tolylene, naphthylene, etc. In addition, R also includes substituted alkylene and arylene radicals as previously defined, such as halosubstituted, for example, chloro, fluoro, etc. Included within the radicals of $R^2$ and $R^3$ are, for example, divalent radicals and trivalent radicals such as

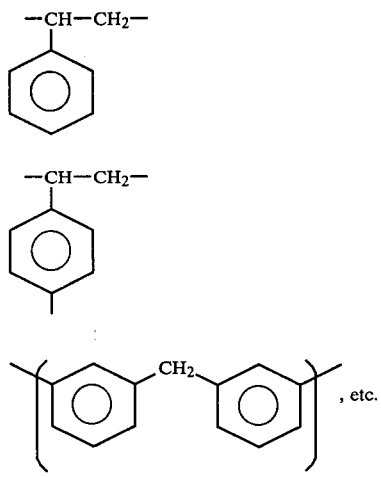

The organoaminodisulfides of formula (1), and hydrohalides thereof are well known materials and can be prepared in accordance with the procedure of T. C. Owen, J. Chem. Soc. (C), 1967, 1373. Included among the organoaminodisulfides of formula (1) are commercially available materials which can be obtained from the Aldrich Chemical Company of Milwaukee, Wis. Some of these organoaminodisulfides of formula (1) are, for example,

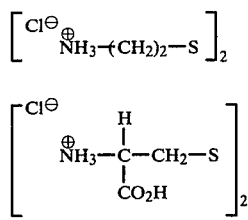

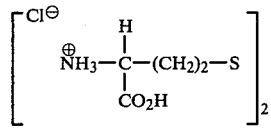

As shown in copending application of Gary R. Faler, Ser. No. 298,711, filed Sept. 2, 1981, organoaminodisulfides of the formula,

where R, X and Y are as previously defined, and $R^1$ is a $C_{(1-8)}$ alkyl radical, also can be used in the practice of the method of the present invention. Some of the organoaminodisulfides of formula (5) are, for example, propylamino-3-propane disulfide, methylamino-2-ethane disulfide, methylamino-3-propane disulfide, etc.

Among the sulfonated aromatic organic polymers consisting essentially of formula (3) units and mixtures of formula (3) and formula (4) units, which can be used in accordance with the practice of the present invention with organoaminodisulfide of formula (1), there are included, for example, Amberlite-118, manufactured by Rohm and Haas Company, Dowex 50W X4, manufactured by Dow Chemical Company, etc., and other sulfonated polystyrenes which have been cross-linked with divinylbenzene.

The modification of the above-described ion-exchange resin with the organoaminodisulfide of formulas (1) and (5) can be accomplished by initially converting the sulfonated aromatic organic polymer consisting essentially of chemically combined formula (3) units to halo-sulfonated units of the formula, $$-R^2- \atop | \atop SO_2X' \qquad (6)$$

where $R^2$, is as previously defined and $X'$ is a halogen radical such as chloro. The halogenation of formula (3) units, can be accomplished by standard procedures such as by use of chlorosulfonic acid, thionyl chloride, etc. The formation of the organoaminomercaptan derivative from the halosulfonated aromatic organic polymer can proceed as follows

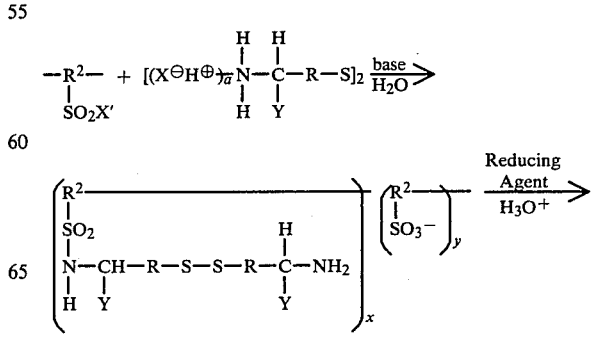

-continued

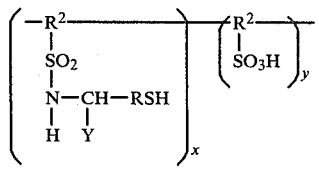

where R, R², and Y are as previously defined and x and y are mole percent ranges within the scope of the present invention.

Reducing agents which can be employed in the practice of the present invention to effect the reduction of the polyaromatic sulfonated organoaminodisulfide derivative are preferably triorganophosphines of the formula, $$(R^4)_3P, \qquad (7)$$

where $R^4$ is selected from a $C_{(4-8)}$ alkyl radical or $C_{(6-13)}$ aryl radical. Some of the triorganophosphines included within formula (7) are, for example, tri-n-butyl phosphine, triphenylphosphine, etc.

In addition to the aforementioned triorganophosphines there can be used as reducing agents, alkali metal borohydrides, for example, sodium borohydrides, and potassium borohydrides. Other reducing agents which can be utilized in the practice of the method of the present invention, are compounds which can effect the reduction of organoaminodisulfide derivatives of sulfonated aromatic organic polymer obtained by using organoaminodisulfide of formula (5). These organoaminodisulfides are shown in the copending application of Gary Faler, Ser. No. 298,711. Reducing agents which can be used to reduce organoaminodisulfide of formula (5), are for example, sodium sulfide, sodium hydroxide/glucose, dissolving alkali metals, for example, sodium, lithium, etc.

In the preparation of the sulfonated aromatic organic polymer having organoaminomercaptan groups covalently attached to sulfone radicals by nitrogen-sulfur linkages, the halosulfonated aromatic organic polymer can be contacted with the organoaminodisulfide of formulas (1) or (5) in the presence of a suitable solvent and a base to produce a disulfide derivative of the aromatic sulfonated organic polymer. Suitable organic solvents which can be used, for example, are water, methanol, ethanol, etc. Bases which can be used in the formation of the disulfide derivative are tertiary organic amines such as triethylamine, pyridine, 4-(N-dimethylamino)-pyridine, trimethylamine, etc. The proportions of the organoaminodisulfide which can be employed will depend on the mole percent substitution of the halosulfonyl radicals on the backbone of the aromatic organic polymer. It has been found that effective results can be achieved if sufficient disulfide is employed to provide at least 0.04 to 2 equivalents of nitrogen per equivalent of halosulfonyl of the ion-exchange resin. Temperatures during the additon reaction can be 25° to 100° C. along with sufficient agitation to facilitate reaction. Preferably, an alkali metal carbonate or bicarbonate, such as sodium bicarbonate, can be employed as the base in place of the tertiary organic amine, which would simultaneously effect disulfide addition while hydrolyzing the excess unreacted halogen on the halosulfonyl radicals.

In instances where organoaminodisulfide of formula (5) is used to make the halosulfonated aromatic organic polymer disulfide derivative, it is preferred to neutralize the organoaminodisulfide if it is in the form of the hydrohalide, with an alkali metal hydroxide, for example, potassium hydroxide, or sodium hydroxide to generate the free amine prior to contacting such organoaminodisulfide with the halosulfonated aromatic organic polymer in the presence of suitable solvent and base as defined above.

The reduction of the cation-exchange resin disulfide bond can be achieved by the use of a reducing agent, for example, triorganophosphine, by mixing the disulfide derivative of the sulfonated organic polymer with the reducing agent. Effective results can be achieved if there are used moles of reducing agent which are at least sufficient to provide a stoichiometric equivalence to moles of the disulfide along the backbone of the sulfonated aromatic organic polymer. In particular situations higher amounts of reducing agent can be employed if desired.

A preferred procedure is to add the reducing agent in the form of an organic solvent solution to a mixture of the disulfide derivative in an aqueous organic solvent. The resulting mixture can thereafter be stirred under ambient temperatures or higher for several hours. The resulting reaction mixture can then be filtered and the recovered ion-exchange resin reaction product can be washed with an alkanol such as methanol, a suitable organic solvent, for example, methylene chloride, and further washed with aqueous hydrochloric acid solution followed by additional washing with organic solvent such as methanol, acetone, etc., followed by drying the resulting product in a drying oven at a temperature in the range of from 50° C. to 110° C.

Analysis of the ion-exchange resin of the present invention consisting essentially of chemically combined units of formulas (2) and (3) can be determined by titration of the residual sulfonic acid with excess 0.1 N NaOH, followed by back titration of the remaining NaOH with 0.1 N HCl. This procedure affords the acid milliequivalency of the acid catalyst. The amount of mercaptan present on the catalyst can be obtained by determining the amount of nitrogen by combustion analysis.

In order that those skilled in the art will be better able to practice the invention, the following examples are given by way of illustration and not by way of limitation.

EXAMPLE 1

A mixture of 1000 ml of anhydrous chloroform, 2622.6 grams of Amberlite-118, a crosslinked sulfonated polystyrene polymer manufactured by the Rohm & Hass Company, and 361.1 grams of chlorosulfonic acid was refluxed with stirring under an atmosphere of nitrogen for a period of three days. The mixture was allowed to cool and the chloroform-chlorosulfonic acid solution was decanted from the remaining resin. The resin was then washed with chloroform. The wet resin was then slowly added to a methanol solution at 5° C. at a rate sufficient to maintain the temperature below 15° C. The resulting mixture was filtered and the resin was washed with cold water, methanol, chloroform, and finally ethylether. After a brief air drying, the resin was dried by azeotropic distillation with heptane, followed by drying in an evacuated oven at 70° C. Based on method of preparation, there was obtained a chlorosulfonated polystyrene resin.

A mixture of 0.5205 gram of the chlorosulfonated resin, about 50 ml of a 0.10 N-sodium hydroxide solution, and 4.45 ml of tetrahydrofuran was refluxed with stirring under an atmosphere of nitrogen for a period of 3 hours. The mixture was then cooled, filtered and the resin was washed with excess amounts of deionized water. The chlorine content of the resulting filtrate was then determined by potentiometric titration using 0.098 N-silver nitrate as the titrant. It was found that the chlorine content of the resin was 15.5% by weight.

There were added 2.7 grams of cystamine dihydrochloride, $S_2(CH_2CH_2NH_2)_2.2HCl$, obtained from the Aldrich Chemical Company, of Milwaukee, Wis., and 25 parts of the above chlorosulfonated polystyrene resin to 350 ml of deionized water which had been preheated to 90° C. The pH of the resulting mixture was adjusted to 9.4 by the addition of sodium carbonate. While heating the reaction mixture to 95° C. additional sodium carbonate was added to the reaction mixture to maintain the pH at 9.4. After about 20 minutes, the pH stabilized and heating was continued for an additional 30 minutes. The resulting cooled ion-exchange resin was removed by filtration and washed with water, followed by methanol.

There was added 5 grams of the above cystamine substituted polystyrene resin to a solution of about 36 ml of methanol and 5 ml of water. There was then added to the resulting mixture 0.3 grams of triphenylphosphine. The resulting mixture was brought to reflux for a period of 4 hours. The cooled reaction mixture was filtered, then the resin was washed with methanol, methylene chloride, a 20% sulfuric acid solution in water, acetone, ether, followed by drying it in an evacuated drying oven at 80° C. Based on method of preparation, there was obtained an ion-exchange resin consisting essentially of about 13 mole percent of sulfonated styrene units having ethylaminomercaptan groups covalently attached to sulfone radicals by nitrogen-sulfur linkages chemically combined with about 87 mole percent of chemically combined sulfonated styrene units.

A mixture of 10 grams of phenol, 1 gram of acetone, and 2 grams of the above ion-exchange catalyst was heated at 70° C. for 1 hour. The mixture was allowed to cool and was diluted with acetonitrile followed by filtration and washing of the catalyst with acetonitrile. The concentration of the filtrate provided a pale yellow liquid which crystallized on standing. There was obtained a mixture of 98% of para,para-bisphenol-A and about 1.4% of ortho,para-bisphenol-A and a conversion of 66.8%, based on high pressure liquid chromatography.

The same procedure was repeated, except that the ion-exchange catalyst utilized was produced by neutralizing the sulfonated polystyrene with 2-mercapto ethyl amine as shown by McNutt et al, U.S. Pat. No. 3,394,089. It was found that the percent conversion of the phenol to bisphenol-A was about 40%.

EXAMPLE 2

Additional sulfonated polystyrene resin having cystamine groups attached to sulfone radicals by nitrogen-sulfur linkages was prepared in a somewhat similar procedure to Example 1. There was employed 20 grams of chlorosulfonated resin which was sufficient to provide 94 milliequivalents of chlorosulfonated styrene units, an equal molar amount of cystamine dihydrochloride, sufficient tetrahydrofuran solvent and a 3 times molar amount of triethylamine as a base condensation catalyst. All the ingredients were stirred together and refluxed at about 70° C. for about 2 hours. The mixture was then filtered and the resin was washed with water, a 10% aqueous hydrochloric acid solution, and additional water. The resulting washed resin was then azeotroped dry with heptane, filtered and then washed with additional heptane and diethylether. The product was then dried in a vacuum oven. Based on method of preparation there was obtained a polystyrene resin consisting essentially of sulfonated polystyrene units chemically combined with sulfonated polystyrene units having aminoethyldisulfide groups covalently attached to sulfone radicals by nitrogen-sulfur linkages.

A mixture of 5 grams of the above sulfonated polystyrene resin having chemically combined sulfonated polystyrene units with covalently bonded aminoethyldisulfide groups, 1 gram of $NaBH_4$ and 25 ml of absolute ethanol was stirred under nitrogen at room temperature for two hours. The mixture was then filtered, and the resin was washed with ethanol, methanol, 10% aqueous hydrochloric acid and then dried azeotropically, filtered, washed with heptane and ether. Based on method of preparation, there was obtained an ion-exchange catalyst consisting essentially of sulfonated polystyrene units chemically combined with styrene units having aminoethylmercaptan groups covalently bonded to sulfone radicals by nitrogen-sulfur linkages.

A mixture of 2 grams of Amberlite-118, 1 gram of the above ion-exchange catalyst having chemically combined sulfonated styrene units with covalently bonded aminoethylmercaptan groups, 1 gram of acetone and 10 grams of phenol was heated at 70° C. The mixture was allowed to cool and then acetonitrile was added to the mixture. The mixture was then filtered, washed with acetonitrile and the filtrate stripped. The ion-exchange catalyst made in accordance with the practice of the present invention was found to be effective as a condensation catalyst for acetone and phenol by providing for the production of bisphenol-A.

EXAMPLE 3

Aminopropyldisulfide within the scope of formula (1) was prepared by oxidizing 3-mercaptopropylamine in accordance with the following procedure:

Hydrogen sulfide was passed through a mixture of 400 ml of methanol and 78 grams of sodium hydroxide until all of the NaOH had dissolved. The resultant solution was heated to 50° C. and 130 grams of 3-chloropropylamine hydrochloride dissolved in 130 ml of methanol was added dropwise. When the addition was complete, the reaction mixture was heated at reflux for an additional hour.

The above cooled reaction mixture was diluted with 300 ml of ethyl ether, followed by filtration and concentration of the filtrate to afford a yellow oil. The yellow oil was distilled at atmospheric pressure and the fraction boiling in the 100°–165° C. range was collected. Toluene was added to the aforementioned fraction and the mixture was azeotropically distilled until the distillate was clear. The hot toluene solution was filtered and the filtrate was allowed to cool at 5° C. where white crystals formed. M.P. 109°–110° C. (Lit. M.P. 108°–109° C.). Based on method of preparation and melting point, there was obtained 3-mercaptopropylamine.

A mixture of 5 grams of the above 3-mercaptopropylamine and 50 ml of dimethylsulfoxide was heated at 105° C. under an oxygen atmosphere for 24 hours. Methylsulfide and excess dimethylsulfoxide were removed by vacuum distillation. There was obtained a residual red oil which was dissolved in methanol. Anhydrous hydrogen chloride was then passed through the solution until the vapors were acid to litmus. The resulting solution was filtered and ethylether was added until the mixture became cloudy. The mixture was allowed to cool to 5° C. resulting in the precipitation of a yellow material. The mixture was then filtered and there was obtained 3.5 parts of a yellow amorphous solid. Based on method of preparation, the solid was aminopropyldisulfide.

A mixture of 50 ml of water, 5 grams of the chlorosulfonated polystyrene of Example 1, 1.04 grams of the above aminopropyldisulfide, and 5.0 grams of sodium bicarbonate was refluxed with stirring for 4 hours. The mixture was then allowed to cool, filtered and the resin was washed with water.

There was added a solution of 5 ml of tri-N-butyl phosphine dissolved in 5 ml of acetone to a mixture of the above sulfonated polystyrene resin having chemically combined aminopropyldisulfide groups, and 50 ml of a 90:10 methanol-water solution. The resulting mixture was allowed to stir at ambient temperature for 5 hours. The resulting sulfonated polystyrene resin was filtered, and washed with methanol, methylene chloride, methanol, 20% HCl, water, methanol, acetone, and diethylether. The resulting product was then dried under reduced pressure at 80° C. and was found to have 3.87 meq/g residual sulfonic acid groups. Based on method of preparation and aforementioned analysis, the product was a polystyrene ion-exchange catalyst having the formula,

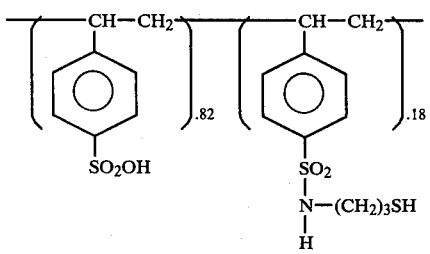

The above catalyst was found to be effective as a condensation catalyst for phenol and acetone in accordance with the previously described procedure.

EXAMPLE 4

In accordance with the procedure of copending application Ser. No. 298,711, filed Sept. 2, 1981, to Gary R. Faler, Method and Catalyst for Making Bisphenol, ion-exchange catalyst was prepared consisting essentially of sulfonated styrene units chemically combined with sulfonated styrene units having propylaminopropylmercaptan groups attached to sulfone radicals by nitrogen-sulfur linkages, as follows:

The intermediate, propyl-3-aminopropanol, was prepared by adding 200 grams of 1-chloro-3-hydroxypropane and 726 grams of N-propylamine to 1600 grams of absolute ethanol. The resulting mixture was heated at reflux for a period of 15 hours. The mixture was then allowed to cool and there was added 127 grams of sodium hydroxide and the reaction mixture was extracted with ether. After drying with magnesium sulfate and removal of the solvent, there was obtained 125.1 grams or a 50% yield of propyl-3-aminopropanol having a boiling point of 70° C. at 1 torr.

There was added to about 124 grams of the above propyl-3-aminopropanol dissolved in 1194 grams of chloroform under an atmosphere of nitrogen and at a temperature of about 0° C., 189 grams of thionyl chloride at a rate which was sufficient to maintain the temperature of the resulting reaction mixture below 20° C. When the addition was complete, the solution was brought to reflux for 30 minutes. The reaction mixture was then quenched with excess ethanol and concentrated to provide a yellow viscous oil. There was obtained a quantitative yield of propylamino-3-chloropropane hydrochloride after the aforementioned yellow viscous oil was crystallized from ethanol in the form of a white crystalline solid; (M.P. 246°-247° C.).

Twenty grams of the above propylamino-3-chloropropane hydrochloride was added to 50 ml of water and the resulting mixture was made basic with a 50% sodium hydroxide solution. The free amine was extracted with chloroform, dried over magnesium sulfate, followed by the removal of the organic solvent which provided a pale yellow oil. The oil was dissolved in 400 ml of absolute ethanol containing 5.0 grams of sodium hydroxide. There was added to this ethanolic solution of the free amine, a solution of 400 grams of ethanol, 3.75 grams of elemental sulfur and 28.1 grams of sodium sulfide nonahydrate which had been refluxed for a period of about 20 minutes. The resulting reaction mixture was then allowed to reflux under an atmosphere of nitrogen. After 15 hours of reflux, the reaction mixture was concentrated on a vacuum evaporator to remove most of the ethanol. The resulting yellow oil was poured into water and the free amino disulfide was extracted with chloroform. The chloroform layer was dried over magnesium sulfate followed by removal of solvent which provided a yellow oil. The yellow oil was then dissolved in ethanol and gaseous hydrogen chloride was bubbled through the solution until the vapors were acidic to moist litmus. Upon cooling, there was obtained a white crystalline solid. The crystalline solid was recrystallized from methanol to provide 14.3 grams or a 72% yield of propylamino-3-propane disulfide dihydrochloride having a melting point of 259°-260° C.

There was added 22 grams of the above propylamino-3-propane disulfide dihydrochloride, 8.8 grams of KOH and 80 grams of sodium bicarbonate to 800 ml of an aqueous methanol solution containing 10% by weight methanol. The resulting solution was allowed to stir at ambient temperature for 20 minutes. There was then added to the solution, 80 grams of polystyrene having 335 milliequivalents of chemically combined sulfonyl chloride and the resulting reaction mixture was stirred at reflux for 4 hours. There was then added to the resulting mixture 40 grams of sodium carbonate and the mixture was heated for an additional hour.

After the mixture was allowed to cool it was filtered. The resulting resin was washed with water followed by methanol. The resin was then added to 800 ml of an aqueous methanol solution having 10% water containing 15.9 grams of tri-n-butylphosphine. The resulting mixture was heated at reflux for 6 hours. The mixture was then filtered and the solids were washed with methanol, acetone, water and a 10% aqueous sulfuric acid solution, followed with additional washing with water. Water was then azeotropically removed from the resulting resin with toluene. The resin was then dried in an evacuated drying oven to remote residual amounts of toluene. Based on method of preparation and elemental analysis for chemically combined nitrogen, there was obtained, assuming a molar equivalence of mercaptan to nitrogen and a starting chlorosulfonated polystyrene substantially free of chemically combined unsulfonated styrene units, an ion-exchange catalyst having the following approximate formula,

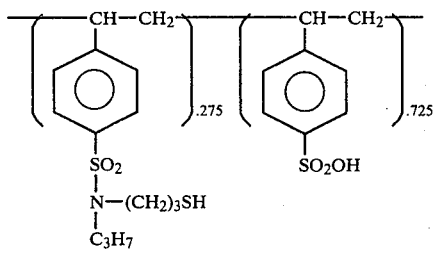

In accordance with the procedure of Example 2, the above ion-exchange catalyst provided a 72% conversion of bisphenol-A, based on the possible theoretical amount which could be formed based on the weight of acetone used.

EXAMPLE 5

There was added to 800 ml of a 90/10 water/methanol solution, 80 grams of sodium bicarbonate, 3.6 grams of potassium hydroxide, and 8.8 grams of propylamino-3-propanedisulfide dihydrochloride. The resulting solution was allowed to stir at ambient temperature for 20 minutes. There was then added to the solution 80 grams of the chlorosulfonated polystyrene prepared in Example 1 and the resulting mixture was heated at reflux for a period of 4 hours. Based on method of preparation, there was obtained a sulfonated polystyrene having chemically combined styrenesulfone units with propylamino-3-propanedisulfide groups attached to sulfur by nitrogen-sulfur linkages.

There was added to the above reaction mixture of the disulfide derivative of sulfonated polystyrene at a temperature of 50° C., 10 ml of a 50% sodium hydroxide solution and 90 grams of sodium sulfide nonahydrate. The resulting heterogeneous mixture was stirred at reflux overnight. The cooled reaction mixture was filtered and the resin was washed with water followed by two liters of a 10% sulfuric acid solution. The resulting washed resin was azeotropically dried with toluene. Based on method of preparation, there was obtained an ion-exchange catalyst consisting essentially of about 15 mole percent of chemically combined sulfonated styrene units having propylamino-3-propane mercaptan groups covalently attached to sulfur by nitrogen-sulfur linkages and about 86 mole percent of sulfonated styrene units. As a condensation catalyst for phenol and acetone in accordance with the procedure of Example 1, this ion-exchange resin was found to provide a 47% conversion to bisphenol-A, based on the weight of acetone.

EXAMPLE 6

There was added 2.4 grams of the aminopropyldisulfide dihydrochloride of Example 3 to 200 ml of a 90:10 water-methanol solution containing 2.6 grams of potassium hydroxide and 20 grams of sodium bicarbonate. The resulting solution was allowed to stir at ambient temperatures at 20 minutes. There was added to this solution 20 grams of the chlorosulfonated polystyrene prepared in Example 1 and the resulting mixture was heated at reflux for a period of 4 hours. Based on method of preparation, there was obtained a sulfonated polystyrene having chemically combined styrenesulfone units with aminopropyldisulfide units covalently attached to sulfur by nitrogen-sulfur linkages.

There was added to the above reaction mixture of the disulfide derivative of sulfonated polystyrene at a temperature of 50° C., 10 ml of a 50% sodium hydroxide solution and 20 grams of sodium sulfide nonahydrate. The resulting heterogeneous mixture was heated at reflux for 3.5 hours. The cooled reation mixture was filtered and the resin was washed with water followed by 1 liter of a 10% sulfuric acid solution. The resulting washed resin was then azeotropically dried with toluene. Based on method of preparation, there was obtained an ion-exchange catalyst consisting of about 20 mole percent of chemically combined sulfonated styrene units having aminopropylmercaptan units covalently attached to sulfur by nitrogen-sulfur linkages and about 80 mole percent of sulfonated styrene units. This ion-exchange resin was found to be an effective condensation catalyst for phenol and acetone to provide for the production of bisphenol-A in accordance with the procedure of Example 1.

Although the above examples are directed to only a few of the very many variables utilized in the practice of the present invention, it should be understood that the present invention is directed to ion-exchange resin consisting essentially of 4 to 40, 5 to 25 mole percent chemically combined units of formulas (2) and (3). The present invention is also directed to a method for making ion-exchange resin utilizing organoaminodisulfide of formulas (1) or (5) and a halosulfonated polyaromatic organic polymer consisting essentially of chemically combined units of formula (6) to produce a polyaromatic organic polymer having organoaminodisulfide groups covalently bonded to sulfone radicals by nitrogen-sulfur linkages followed by the reduction of such sulfonated polyaromatic disulfide derivative with a reducing agent to produce sulfonated aromatic organic polymer having organomercaptan groups covalently bonded to sulfone radicals by nitrogen-sulfur linkages.

What we claim as new and desire to secure by Letters Patent of the United States is:

1. A method for making a leach resistant organoaminomercaptan substituted sulfonated aromatic organic polymer which comprises,
   (1) effecting reaction between
      (A) a halosulfonated aromatic organic polymer and
      (B) an organoaminodisulfide selected from the class consisting of

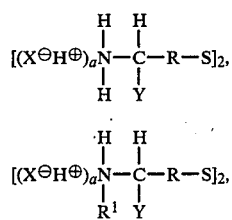

and mixtures thereof, in the presence of base to produce a sulfonated aromatic organic polymer having organoaminodisulfide groups covalently bonded to sulfonyl radicals by nitrogen-sulfur linkages, (2) effecting the reduction of the organoaminodisulfide groups on the sulfonated aromatic organic polymer of (1), and (3) recovering sulfonated aromatic organic polymer from (2) having covalently bonded organoaminomercaptan groups attached sulfonyl radicals by nitrogen-sulfur linkages, where R is a divalent $C_{(1-13)}$ organic radical, Y is selected from the class consisting of hydrogen, carboxy and nitrile, X is selected from the class consisting of halogen or a counter ion, $R^1$ is a $C_{(1-8)}$ alkyl radical and a is 0 or 1.

2. A method for making an organoaminomercaptan substituted sulfonated aromatic organic polymer which comprises, (1) effecting reaction between (A) a halosulfonated aromatic organic polymer and (B) an organoaminodisulfide selected from the class consisting of

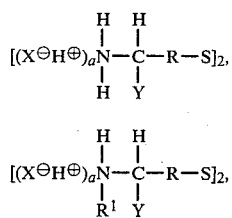

and mixtures thereof, in the presence of base to produce a disulfide derivative, (2) treating the disulfide derivative of (1) with an effective amount of a triorganophosphine which is sufficient to convert the disulfide derivative to sulfonated aromatic organic polymer having organoaminomercaptan groups covalently attached to sulfone radicals by nitrogen-sulfur linkages, (3) recovering the resulting sulfonated aromatic organic polymer from the mixture of (2), where R is a divalent $C_{(1-13)}$ organic radical, Y is selected from the class consisting of hydrogen, carboxy and nitrile, X is selected from the class consisting of halogen or a counter ion, $R^1$ is a $C_{(1-8)}$ alkyl radical and a is 0 or 1.

3. A method in accordance with claim 1, where the halosulfonated aromatic organic polymer is chlorosulfonated polystyrene.

4. A method in accordance with claim 1, where the organoaminodisulfide has the formula

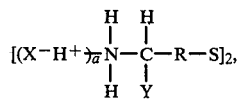

where R is a $C_{(1-13)}$ divalent organic radical, X is a halogen radical or counterion, Y is selected from hydrogen, carboxy and nitrile and a is 0 or 1.

5. A method in accordance with claim 1, where the reduction of the organoaminodisulfide group on the sulfonated aromatic organic polymer is effected with a triorganophosphine.

6. A method in accordance with claim 1, where the reduction of the organoaminodisulfide group on the sulfonated organic polymer is effected with an alkali metal borohydride.

7. A method in accordance with claim 1, where the reduction of the organoaminodisulfide group on the sulfonated organic polymer is effected with an alkali metal sulfide.

8. A method in accordance with claim 1, where the reduction of the organoaminodisulfide group on the sulfonated organic polymer is effected with sodium sulfide.

9. A method in accordance with claim 1, where the triorganophosphine is triphenylphosphine.

10. A method in accordance with claim 1, where the triorganophosphine is tributylphosphine.

11. Sulfonated aromatic organic polymer consisting essentially of units of the formula,

chemically combined with units of the formula,

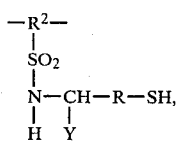

which is effective as a bisphenol catalyst based on phenol-ketone condensation, where R is a divalent $C_{(1-13)}$ organic radical, $R^2$ is a trivalent $C_{(6-13)}$ aromatic organic radical, and Y is selected from hydrogen, carboxy and nitrile.

12. A sulfonated aromatic organic polymer in accordance with claim 11, having from about 4 mole percent to 40 mole percent of chemically combined units of the formula,

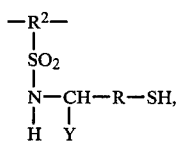

where R is a divalent $C_{(1-13)}$ organic radical, $R^2$ is a trivalent $C_{(6-13)}$ aromatic organic radical, and Y is selected from hydrogen, carboxy and nitrile.

13. An ion-exchange resin comprising sulfonated polyaromatic organic material having from about 5 to about 25 mole percent of divalent chemically combined organoaminomercaptan sulfonated aromatic organic units of the formula,

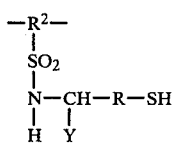

based on the total moles of chemically combined aromatic organic units in the material, where R is a divalent $C_{(1-13)}$ organic radical, Y is a monovalent radical selected from hydrogen, carboxy, and nitrile, and $R^2$ is a trivalent $C_{(6-13)}$ aromatic organic radical.

14. An ion-exchange resin in accordance with claim 13, where the sulfonated polyaromatic organic material is a sulfonated aromatic organic polymer consisting essentially of divalent sulfonated aromatic organic units of the formula, $$\begin{array}{c} -R^2- \\ | \\ SO_2OH \end{array}$$

blended with sulfonated aromatic organic polymer consisting essentially of such divalent sulfonated aromatic organic units chemically combined with divalent aromatic units of the formula, $$\begin{array}{c} -R^2- \\ | \\ SO_2 \\ | \\ N-CH-R-SH, \\ | \phantom{-CH-}| \\ H \phantom{-CH-}Y \end{array}$$

where R is a divalent $C_{(1-13)}$ organic radical, $R^2$ is a trivalent $C_{(6-13)}$ aromatic organic radical, and Y is selected from hydrogen, nitrile, and carboxy.

15. An ion-exchange resin in accordance with claim 13, where the polyaromatic organic material is an organic polymer consisting essentially of sulfonated styrene units chemically combined with sulfonated styrene units having aminoethylmercaptan groups attached to sulfone radicals by covalent nitrogen-sulfur linkages.

16. An ion-exchange resin in accordance with claim 13, where the polyaromatic organic material is an organic polymer consisting essentially of sulfonated styrene units chemically combined with sulfonated styrene units having aminopropylmercaptan groups attached to sulfone radicals by covalent nitrogen-sulfur linkages.

* * * * *